United States Patent
Carpenter et al.

(10) Patent No.: US 7,811,550 B2
(45) Date of Patent: *Oct. 12, 2010

(54) METHOD FOR MAKING MAGNETIC FLUORESCENT CORE SHELL NANOPARTICLES

(75) Inventors: Everett E. Carpenter, Silver Spring, MD (US); Vincent Carpenter, Laurel, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 1052 days.

This patent is subject to a terminal disclaimer.

(21) Appl. No.: 11/444,818

(22) Filed: May 19, 2006

(65) Prior Publication Data

US 2007/0111020 A1    May 17, 2007

Related U.S. Application Data

(62) Division of application No. 10/414,571, filed on Apr. 15, 2003, now Pat. No. 7,235,228.

(51) Int. Cl.
*A61B 5/055* (2006.01)

(52) U.S. Cl. .................... 424/9.32; 424/1.29; 424/1.37; 424/489

(58) Field of Classification Search ................ 424/1.11, 424/1.29, 1.33, 1.61, 1.65, 1.81, 9.1, 400, 424/451, 455, 457, 458, 459, 463, 489, 490, 424/9.3, 9.32, 9.36, 1.37; 428/402, 402.24, 428/403; 252/301.4 R, 301.6 R, 301.6 S, 252/301.6 P, 301.6 F, 301.4 S, 301.4 P, 301.4 F
See application file for complete search history.

(56) References Cited

U.S. PATENT DOCUMENTS 7,235,228 B2 * 6/2007 Carpenter et al. .......... 424/9.32

OTHER PUBLICATIONS

Tian et al (J. Phys. Chem., 1996, vol. 110, No. 21, pp. 8927-8939).*

* cited by examiner

*Primary Examiner*—D L Jones
(74) *Attorney, Agent, or Firm*—Amy Ressing; Stephen T. Hunnius

(57) ABSTRACT

This invention comprises nanoparticles for use with biosensors. The nanoparticles have core/shell architecture. The nanoparticles can be detected by two means, magnetic and optical by virtue of the nanoparticles magnetic core and fluorescent semiconductor shell. Methods of making the nanoparticles and their composition are described.

13 Claims, 4 Drawing Sheets

CdS@FeO$_x$ TEM

- Oblate aggregates of 3nm particles
- Aggregate size a function of sample preparation
- Magnetic moment very low at ~10 emu/g

US 7,811,550 B2

METHOD FOR MAKING MAGNETIC FLUORESCENT CORE SHELL NANOPARTICLES

This application is a divisional application of U.S. application Ser. No. 10/414,571 filed on Apr. 15, 2003 now U.S. Pat. No. 7,235,228, incorporated herein by reference.

BACKGROUND OF THE INVENTION

1. Field of the Invention

This invention is in the area of biosensors, and encompasses nanoparticles whose presence is detectable by two means, magnetic and visual. The nanoparticles have a core/shell structure with a magnetic core and a fluorescent semiconductor shell.

2. Description of Background Art

Passivated magnetic nanoparticles with core shell structure have recently been described in U.S. patent application Ser. No. 10/355,162 filed on Jan. 31, 2003 and based on provisional U.S. patent application 60/307,693 filed Apr. 4, 2002 by the inventors of this patent application, both applications are incorporated herein by reference in their entirety. In the invention described in the incorporated patent applications, nanoparticles having a core/shell structure with a magnetic core and a metal oxide shell are described and claimed. The shell passivates the core to protect against further oxidation.

U.S. Pat. No. 6,048,515 describes multilayered nanoparticles having a magnetic core and at least two layers of coatings thereon. The particles of this invention may be detected magnetically or visually because of the reddish brown color of the core. The nanoparticles of this invention are said to be useful for diagnostic and therapeutic purposes.

OBJECTS OF THE INVENTION

An object of this invention is to produce core/shell structured nanoparticles having properties which provide for more than one manner of detection. The properties are magnetic detection by virtue of the nanoparticles magnetic core, and visual detection by virtue of the particles fluorescent semiconductor or a surface plasma resonances in the outer shell.

Another object of this invention is to provide a new diagnostic tool.

Another object of this invention is to provide a synthesis route for magnetic/fluorescent nanoparticles.

Another object of this invention is to provide nanoparticles with dual detection properties for use in biomedical applications and biodetection schemes.

SUMMARY OF THE INVENTION

Magnetic nanoparticles based on iron oxide core have been synthesized in a variety of methods including sonochemical, photochemical, as well as other solution chemical methods. Using the reverse micelle system it is possible to form a shell semiconductor layer that makes the magnetic nanoparticles fluoresce. This semiconductor layer then adds to the applicability of the particle by altering the electronic properties of the particle while maintaining the magnetic properties of the core. For biomedical applications this semiconductor layer provides an additional fluorescence without further functionalization. As a result, the core/shell nanoparticles can be used in a variety of biological applications where their magnetic properties are most desirable.

The advantages of using chemical routes to produce the core/shell magnetic/fluorescent nanoparticles of this invention include the ability to produce larger quantities of material while achieving better chemical homogeneity due to mixing of the constituents at the molecular level.

The focus of this synthesis was the development of a magnetic nanoparticle which also has fluorescent properties. To this end, this invention expands on core/shell synthesis to now grow a semiconductor shell. The semiconductor, CdS, CdSe and other group III and group V fluorescent semiconductors give the nanoparticles of the invention fluorescent properties while maintaining the magnetic properties of the core.

The advantages of the synthesis comes in two parts, first it allows for the construction of a hybrid magnetic semiconductor which can be used in dual detection schemes, both optically and magnetically. The use of a QDot (nanoparticle semiconductor) has many advantages over traditional dyes, such as narrower emission and excitation bands and resistance to photobleaching.

Currently, in linear flow assays using colloidal nanoparticles, the nanoparticles travel with the solvent front through a porous membrane to a conjugated pad. Here the functionalized nanoparticles stick giving a visual qualitative reading of whether an analyte is present or not. Using this technique in the field, a Corpman could use the visual detection of a test strip for various biological agents. In cases where the visual detection and evaluation might be ambiguous, the magnetic properties would not be. The same test strip could be sent to a field hospital where technicians could use a magnetic strip reader and quantify the results.

DETAILED DESCRIPTION OF THE INVENTION

In this invention, metal salts of Fe, Co or Ni or other ferromagnetic metals or alloys thereof or mixtures thereof were dissolved within the aqueous core of a reverse micelle system formed using surfactants in organic solvents. The surfactants used in the micelle system are quateranary ammonium salts, polyoxylethoxylates, and sulfate esters. Examples of surfactants are cetyltrimethylammonium bromide, nonyphenolpolyethoxylate 4 and 7 (NP-4 and NP-7), sodium dodecylbenzenesulfonate, and bis(2-ethylhexyl)sulfosuccinic ester. Organic solvents used include chloroform, toluene or any organic solvent compatible with the surfactant and micelle synthesis system.

In practice, the metal salt solution which will form the nanoparticle core is mixed with the organic surfactant solution to form the micelle solutions. A sodium borohydride reducing solution is also mixed with organic surfactant solution. The two micelle solutions are mixed and allowed to react to effect reduction of the metal salt to the core ferromagnetic metal. As well as sodium borohydride, lithium borohydride may also be used as can any equivalent reducing agent.

Figure 1:
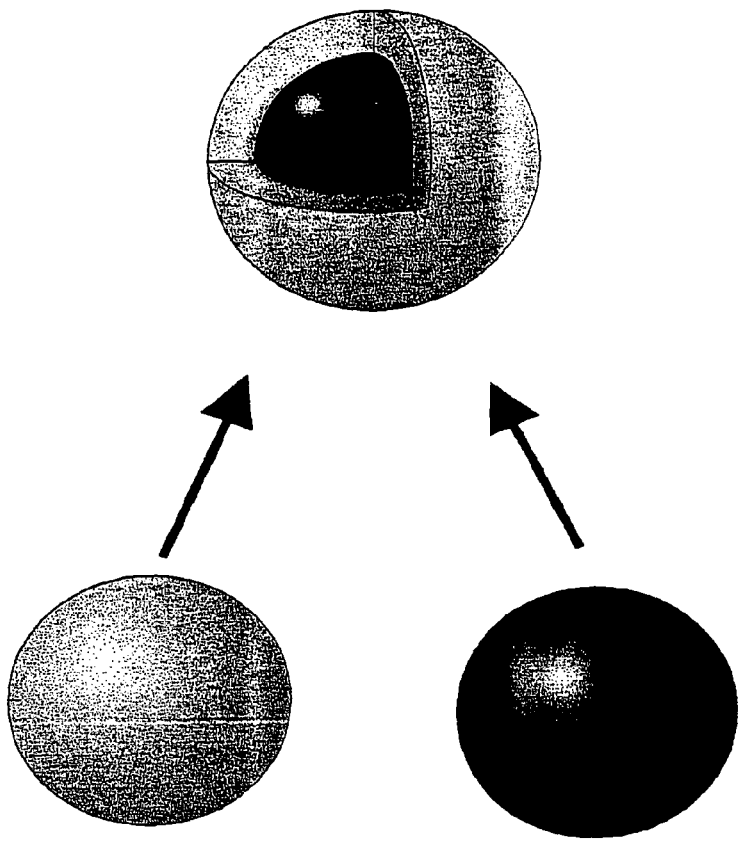
FIG. 1. shows the core/shell structure of the invention.
Figure 2:
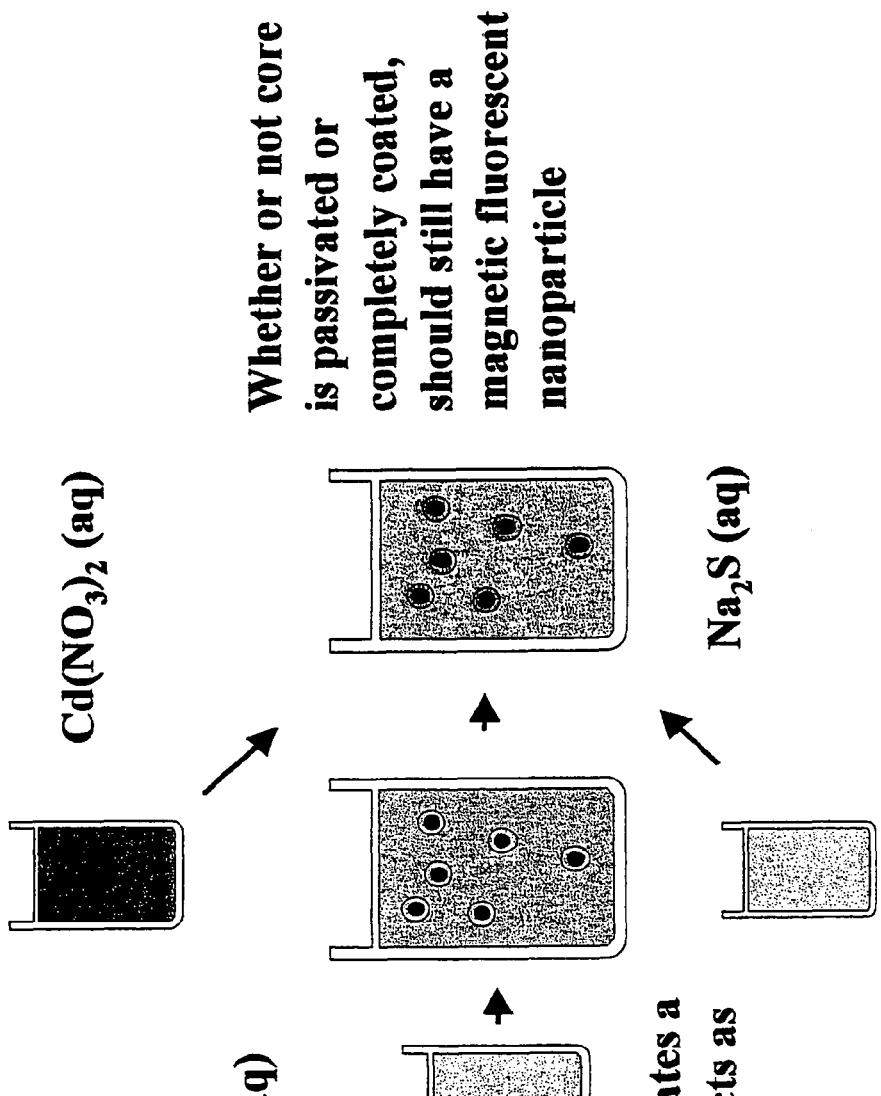
FIG. 2. shows the general synthesis route for the invention.

Following isolation of the core magnetic nanoparticles, the nanoparticles are treated with a metal sulfide such as sodium sulfide or equivalents thereof which results in formation of metal sulfide monolayer on the surface of the core material which act as seed for epitaxial growth of the fluorescent semiconductor shell layer. To form the shell, sodium sulfide and the fluorescent semiconductor precursor are alternatively added to the sodium sulfide treatment mixture. This synthetic procedure is outlined in FIG. 2. The semiconductor precursor is a salt of the semiconductor such as a nitrate which is added alternatively with sodium sulfide to the sulfide treated core material to form the fluorescent semiconductor. Semiconductors useful in this invention are CdS, CdSe, And other fluorescent semiconductors of group III or group V.

It must be recognized that during isolation and reaction of the magnetic core metal nanoparticles, some of the magnetic nanoparticles may be oxidized to metal oxide so that the core material may indeed be ferrimagnetic, as demonstrated for iron, Fe, $Fe_3O_4$ and or $MFe_2O_4$ where M is Fe, Co, or Ni. Also it must be recognized that the whole core/shell structure may be a gradient composite material of Fe(FeO)FeSCdS. However, the end result is the same, a nanoparticle with a magnetic core and a fluorescent semiconductor shell.

In this invention, the preferred fluorescent semiconductors are cadmium sulfide (CdS), and cadmium selenide (CdSe). Other suitable fluorescent semiconductors for use in the invention are semiconductors of group V and group III with fluorescent properties. The magnetic metal core diameter ranges from about 2 to about 50 nm, while the shell thickness ranges from about 0.5 to about 50 nm. The core materials are selected to be a ferrimagnetic metal oxide or a ferromagnetic metal. The ferrimagnetic oxides include $Fe_3O_4$, or $MFe_2O_4$ where M is Fe, Co, or Ni and the ferromagnetic metals include Fe, Co, or Ni or alloys thereof or mixtures thereof. The core is coated with CdS or CdSe or equivalents thereof or mixtures thereof to provide fluorescent semiconductor nanoparticles.

Figure 4:
FIG. 4. shows TEM of CdS-FeO$_x$ aggregates of 3 nm nanoparticles.

Dynamic light scattering as well as transmission electron microscopy (TEM) is used to determine particle size. FIG. 4. shows a TEM micrograph of aggregates of 3 nm particles of core/shell nanoparticles of CdS shell over an $FeO_x$ core. Composition of the nanoparticles is determined by inductively coupled plasma, and the nature of the core is determined by x-ray absorption fine structure measurement.

The magnetic properties of the nanoparticles of this invention are determined using s SQUID magnetometer over a temperature range of 10K-300K. The particles have a magnetization of ~11-15 emu/g at 100 G. Due to the large diamagnetic contribution from the semiconductor, the magnetization decreases as the field increases.

Figure 3:
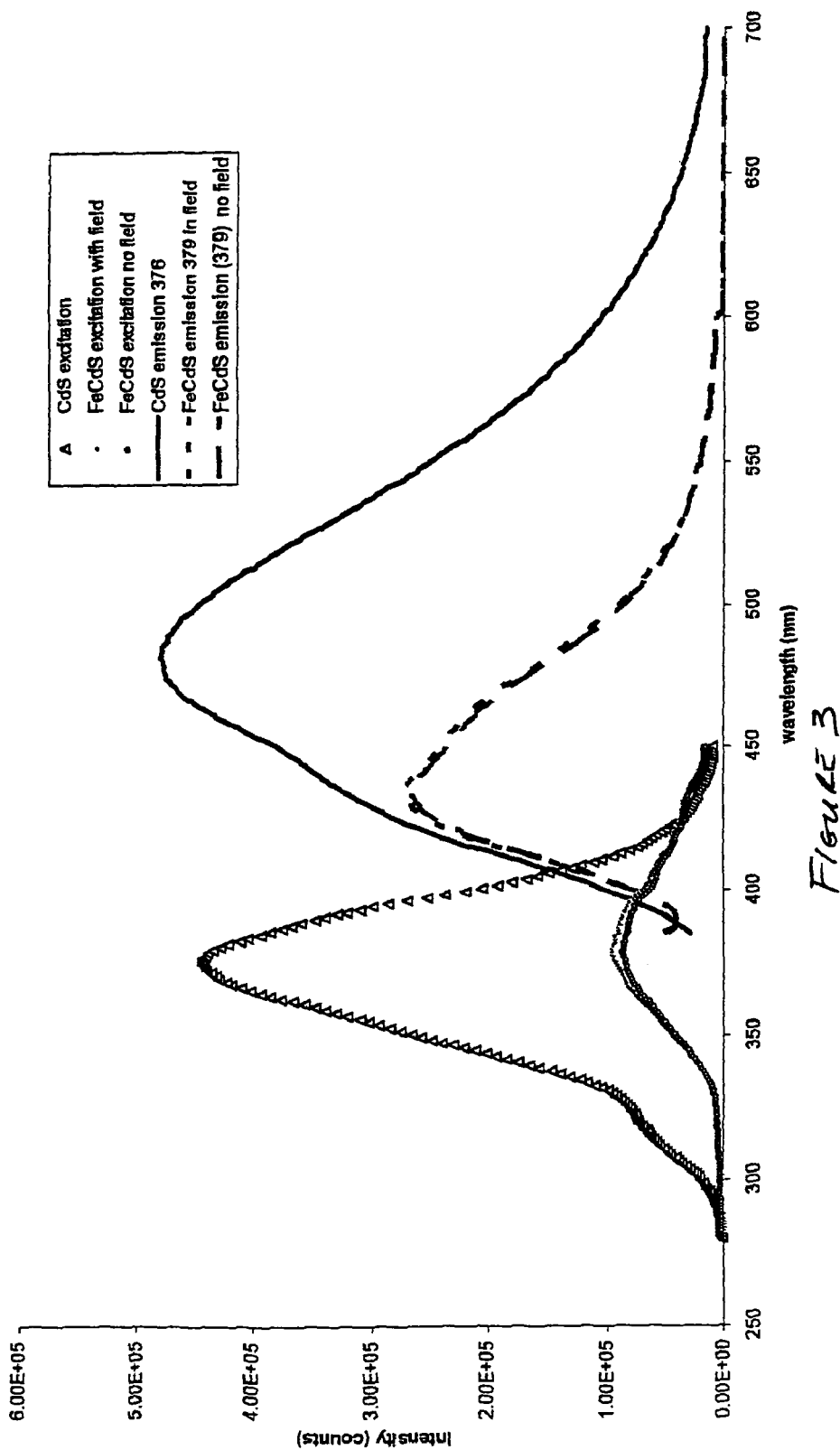
FIG. 3. shows fluorescence spectra of semiconductor and iron semiconductor materials.

Fluorescent properties of the nanoparticles of this invention are measured using a spectrofluorometer over a wavelength of 280-450 nm for excitation scans and 380-750 nm for emission scans. FIG. 3. demonstrates that the fluorescent properties of the nanoparticles of the invention are very similar to micelle generated CdS nanoparticles. Thus the core/shell nanoparticles of this invention possess fluorescent properties similar to the semiconductor, with the added property of a magnetic signal. Typically fluorescence detection has the disadvantage of suffering from false readings due to photobleaching and other effects. The added magnetic detection feature allows for clinical verification without further sampling or sample preparation. FIG. 3. shows the spectral results of six experiments comparing fluorescent semiconductors (Qdots) with Qdot coated magnetic particles. Parenthetically, results show a 10% increase in fluorescence due to the presence of an external magnetic field. At the left of FIG. 3. is shown tracings of excitation scans and on the right are shown tracings of emission scans. In an excitation scan, the emission monochromater is held fixed while the excitation monochromater is scanned. In an emission scan the reverse takes place, excitation monochromator is held fixed and the emission monochromater is scanned.

FIG. 3. shows the spectral results of six experiments comparing fluorescent semiconductors (Qdots) with Qdot coated magnetic particles. Parenthetically, results show a 10% increase in fluorescence due to the presence of an external magnetic field. At the left of FIG. 3. is shown tracings of excitation scans and on the right are shown tracings of emission scans. In an excitation scan, the emission monochromater is held fixed while the excitation monochromater is scanned. In an emission scan the reverse takes place, excitation monochramater is held fixed and the emission monochromater is scanned.

Synthesis

Colloidal nanoparticles of iron were synthesized using reverse micelles. 219 mg iron (II) chloride dissolved in 1.6 ml deionized water was used as the aqueous core precursor. 191 mg sodium borohydride was dissolved in 1.5 ml of deionozed water for use as the reducing agent. The surfactant solution was prepared using 28.0 grams of cetyltrimethylammonium bromide (CTAB) dissolved in 200 ml chloroform. The aqueous metal solution was mixed with 50 ml CTBA solution and placed in a flask under flowing nitrogen. The sodium borohydride solution was mixed with 50 ml CTAB solution for 4 minutes to degas and homogenize. The sodium borohydride/CTAB solution was added to the iron chloride/CTAB and allowed to react with magnetic stirring under flowing nitrogen for 45 minutes.

To 0.05 gm of colloidal iron nanoparticle was added 0.01 M sodium sulfide, the amount add depends on the amount of metal colloide being used.

Following the sulfide addition, alternative additions of ~0.1 M cadmium nitrate and sodium sulfide were made until 3 ml of each was added. Because of low solubilities there is virtually no free CdS in solution and this results in shell growth rather than nucleation. The reaction products are recovered using magnetic separation.

Colloidal cadmium selenide for use as a shell material was synthesized by the methods reported by Tian et al. *J. Phys. Chem.* 1996, 100, 8927-8939; and Kortan et al. *J. Am. Chem. Soc.* 1990, 112, 1327-1332; both references incorporated herein by reference. The colloidal CdSe was then used in shell synthesis as outlined above.

The invention claimed is:

1. A method for making a hybrid magnetic semiconductor having a magnetic metal core and fluorescent semiconductor shell structure, comprising:
   (a) making a micelle composition by mixing an aqueous ferromagnetic metal salt solution and a surfactant in an organic solvent;
   (b) making a micelle composition by mixing an aqueous reducing agent solution and a surfactant in an organic solvent;
   (c) mixing the micelle compositions of (a) and (b) wherein the reduction of said metal salt to said magnetic metal core is effected;
   (d) functionalizing said magnetic metal core by treating with a sulfide to form metal sulfide seed crystals;
   (e) reacting said functionalized magnetic metal core with a fluorescent semiconductor material to form a fluorescent semiconductor shell on said magnetic metal core; and
   (f) resulting in a hybrid magnetic semiconductor having a magnetic metal core and fluorescent semiconductor shell structure.

2. The method according to claim 1, wherein said magnetic metal core is selected from the group consisting of ferromagnetic metals or ferromagnetic metal oxides or alloys thereof or mixtures thereof.

3. The method according to claim 2, wherein said ferromagnetic metal is selected from the group consisting of Fe, Co, or Ni or alloys thereof.

4. The method according to claim 2, wherein said ferromagnetic oxide is selected from the group consisting of $Fe_2O_3$ or $MFe_2O_4$ wherein M is selected from the group consisting of Fe, Co, Ni, and combinations thereof.

5. The method according to claim 1, wherein said fluorescent semiconductor is selected from the group consisting of CdS, CdSe, or other group III or group V semiconductors.

6. The method according to claim 1, wherein said surfactants is selected from the group consisting of quaternary ammonium salts, polyoxyethoxylates, or sulfate esters.

7. The method according to claim 1, wherein said surfactants are selected from the group consisting of cetyltrimethylammonium bromide, nonylphenolpolyethoxylate 4 and 7, sodium dodecylbenzenesulfonates or bis(2-ethylhexyl)sulfosuccinic ester.

8. The method according to claim 1, wherein said reducing agent is selected from the group consisting of Na or $LiBH_4$ or equivalents thereof.

9. A composition of matter prepared according to any of claim 1 or 2-8 above.

10. A hybrid magnetic semiconductor, comprising: nanoparticles having a magnetic core and fluorescent semiconductor shell structure, said core comprising one selected from the group consisting of a magnetic metal, a magnetic metal oxide, alloys thereof, and mixtures thereof wherein said magnetic metal is selected from the group consisting of Fe, Co, or Ni and said shell being a fluorescent semiconductor.

11. The composition according to claim 10, wherein said nanoparticles have a diameter of up to about 100 nm.

12. The composition according to claim 10, wherein said core has a diameter of about 5-50 nm, and said shell has a thickness of about 0.5-50 nm.

13. The composition according to claim 10, wherein said magnetic metal oxide is selected from the group consisting of $Fe_2O_3$ or $MFe_2O_4$.

* * * * *